(12) United States Patent
Pena

(10) Patent No.: US 10,238,523 B2
(45) Date of Patent: Mar. 26, 2019

(54) FOOT DROP COUNTERING ASSEMBLY

(71) Applicant: Antonio Pena, Joliet, IL (US)

(72) Inventor: Antonio Pena, Joliet, IL (US)

( * ) Notice: Subject to any disclaimer, the term of this patent is extended or adjusted under 35 U.S.C. 154(b) by 362 days.

(21) Appl. No.: 15/154,356

(22) Filed: May 13, 2016

(65) Prior Publication Data

US 2017/0325986 A1    Nov. 16, 2017

(51) Int. Cl.
*A61F 5/01* (2006.01)

(52) U.S. Cl.
CPC ................. *A61F 5/0113* (2013.01)

(58) Field of Classification Search
CPC ..... A61F 5/0113; A61F 5/0111; A61F 5/0116; A61F 5/3769; A61F 5/3776; A61F 5/3792; A63B 23/08; A63B 23/085; A63B 21/04; A63B 21/0407; A63B 21/0442; A63B 21/0557; A43C 7/00; A43C 7/04; A43C 7/08

See application file for complete search history.

(56) References Cited

U.S. PATENT DOCUMENTS

| | | | |
|---|---|---|---|
| 1,608,032 A * | 11/1926 | McNabb | A61F 5/0104 602/30 |
| 2,584,010 A * | 1/1952 | Goffredo | A61F 5/0113 602/28 |
| 3,986,501 A * | 10/1976 | Schad | A61F 5/0111 602/28 |
| 4,329,982 A * | 5/1982 | Heaney | A61F 5/0113 602/28 |
| 4,566,447 A * | 1/1986 | Deis | A61F 5/0113 602/28 |
| 4,817,589 A | 4/1989 | Wertz | |
| 4,930,767 A * | 6/1990 | Hamm | A63B 21/0552 482/124 |
| 5,382,224 A * | 1/1995 | Spangler | A61F 5/0113 602/23 |
| 7,125,392 B2 * | 10/2006 | Scott | A61F 5/0113 602/23 |
| 7,354,413 B2 | 4/2008 | Fisher | |
| 7,458,950 B1 * | 12/2008 | Ivany | A43B 7/14 36/136 |
| D629,913 S | 12/2010 | Beckwith et al. | |
| 2002/0129821 A1 * | 9/2002 | Trieloff | A61F 5/0113 128/882 |
| 2005/0070833 A1 * | 3/2005 | Shields | A61F 5/0113 602/27 |
| 2007/0100268 A1 * | 5/2007 | Fisher | A61F 5/0113 602/28 |
| 2008/0077066 A1 * | 3/2008 | Lewis | A61F 5/0113 602/28 |
| 2008/0154166 A1 * | 6/2008 | Beckwith | A61F 5/0113 602/27 |
| 2010/0076361 A1 * | 3/2010 | Kruijsen | A61F 5/0113 602/28 |
| 2011/0082404 A1 * | 4/2011 | Wenger | A61F 5/0111 602/28 |

(Continued)

*Primary Examiner* — Kari Rodriquez

(57) ABSTRACT

A foot drop countering assembly includes a band that is configured to extend around a person's leg below and adjacent to a knee of the leg. A tether has a first end and a second end. The first end is attached to the band. An engagement member is attached to the second end of the tether. The engagement member is configured to engage a person's foot to pull the foot upwardly towards the knee.

5 Claims, 5 Drawing Sheets

(56) References Cited

U.S. PATENT DOCUMENTS

| | | | | |
|---|---|---|---|---|
| 2012/0029401 A1* | 2/2012 | Caldwell | ............... | A61F 5/0113 602/16 |
| 2013/0172801 A1* | 7/2013 | Hatzis | ................... | A61F 5/0127 602/27 |
| 2014/0276320 A1* | 9/2014 | Faux | ..................... | A61F 5/0113 602/28 |
| 2015/0374527 A1* | 12/2015 | Wenger | ................. | A61F 5/0113 602/28 |

* cited by examiner

FOOT DROP COUNTERING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIE THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to foot lifting devices and more particularly pertains to a new foot lifting device for assisting a person with drop foot by lifting the front portion of their foot upwardly such that it does not drag on a ground surface while the person is walking.

BRIEF SUMMARY OF THE INVENTION

An embodiment of the disclosure meets the needs presented above by generally comprising a band that is configured to extend around a person's leg below and adjacent to a knee of the leg. A tether has a first end and a second end. The first end is attached to the band. An engagement member is attached to the second end of the tether. The engagement member is configured to engage a person's foot to pull the foot upwardly towards the knee.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
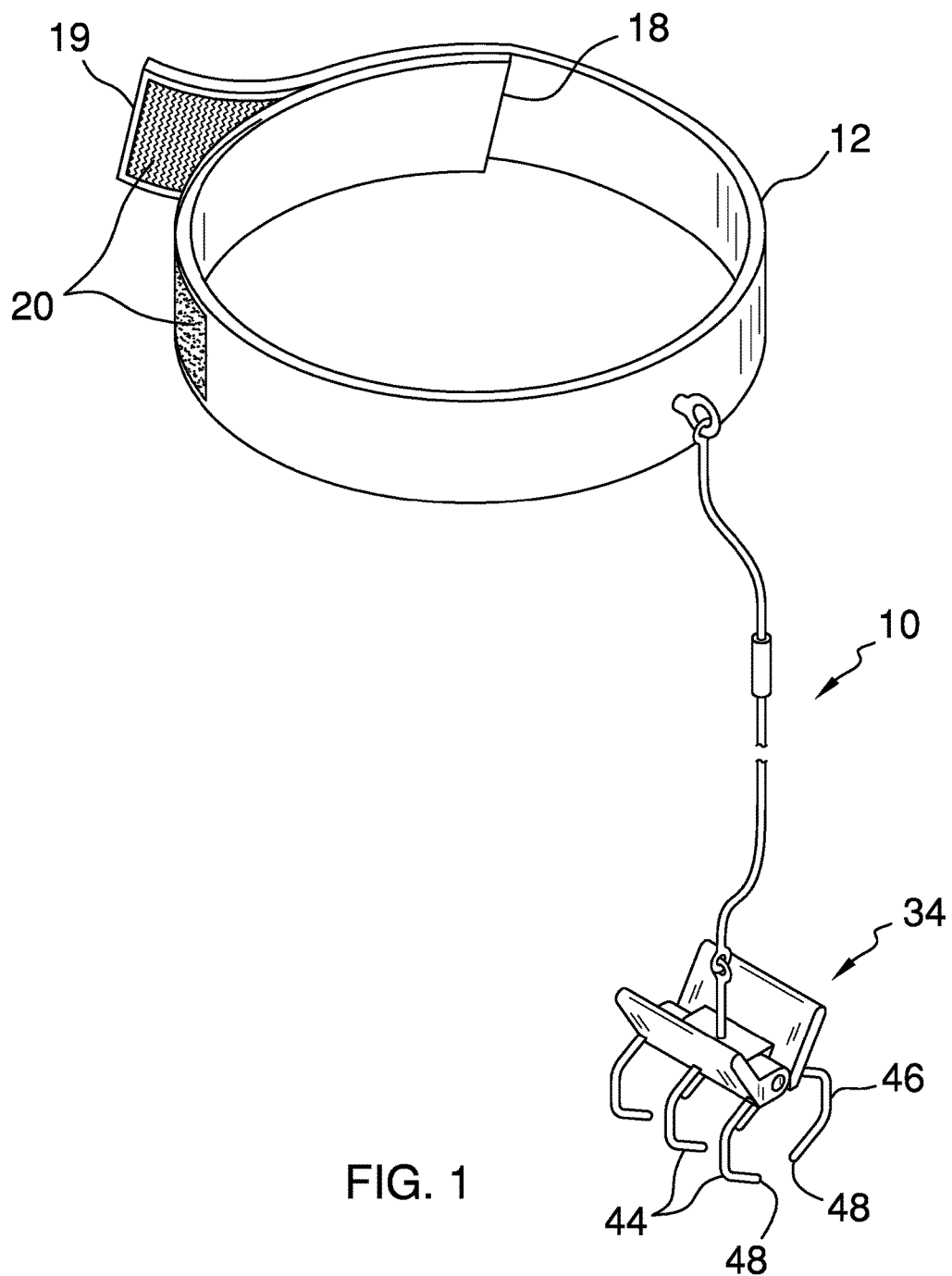
FIG. 1 is a front perspective view of a foot drop countering assembly according to an embodiment of the disclosure.
Figure 2:
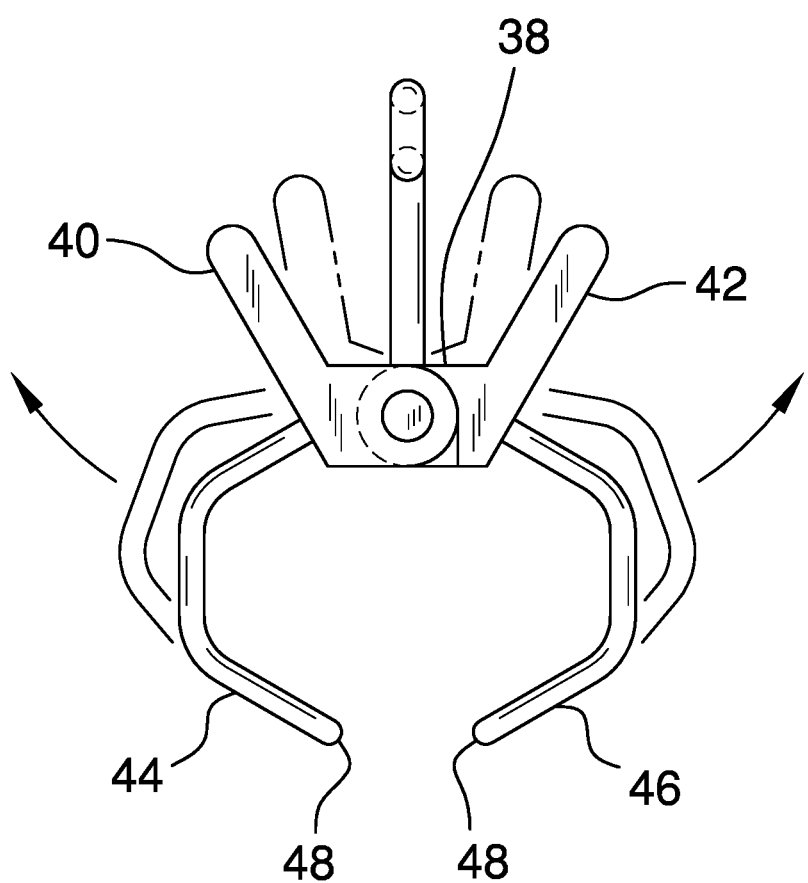
FIG. 2 is a front view of an of an engagement member of an embodiment of the disclosure.

With reference now to the drawings, and in particular to FIGS. 1 through 5 thereof, a new foot lifting device embodying the principles and concepts of an embodiment of the disclosure and generally designated by the reference numeral 10 will be described.

As best illustrated in FIGS. 1 through 5, the foot drop countering assembly 10 generally comprises a band 12 that is configured to extend around a person's leg 14 below and adjacent to a knee 16 of the leg 14. The band 12 is formed into a closed loop configuration having an adjustable circumference. As such, the band 12 may have a pair of free ends 18, 19 and a coupler 20 is attached to the band 12 and is configured to retain the band 12 in the closed loop configuration. The coupler 20 may comprise a hook and a loop coupler as shown in FIG. 1, however other couplers, such as buckles, snaps and buttons may also be utilized.

A tether 22 has a first end 24 and a second end 26. The first end 24 is attached to the band 12 and the tether 22 may be resiliently stretchable. The tether 22 may have an adjustable length wherein the tether includes a first portion 28 and a second portion 30 attached together with connector 32. The first 28 and second 30 portions may be cut to the desired length before attachment together with the connector 32.

Figure 4:
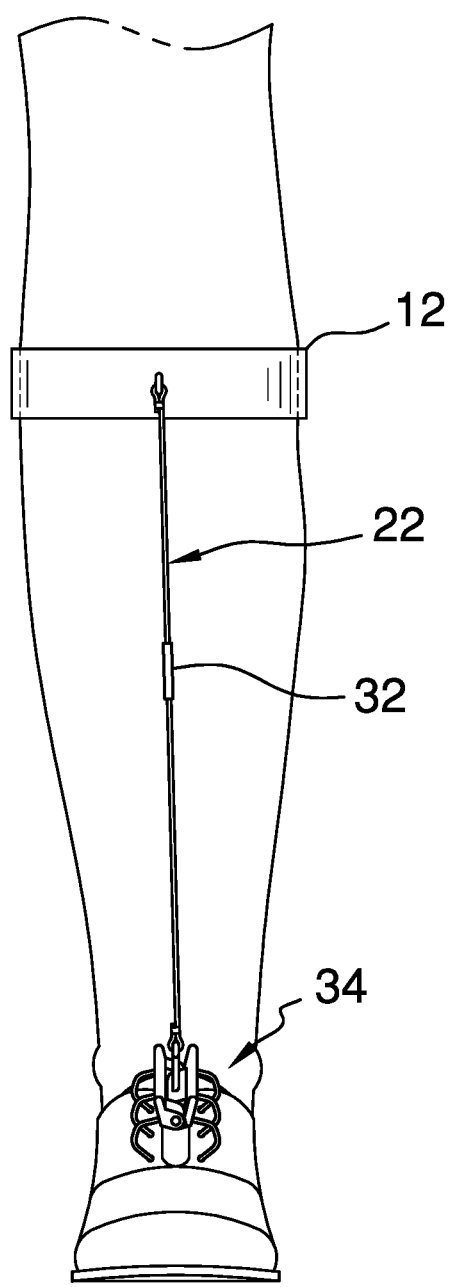
FIG. 4 is a front in-use view of an embodiment of the disclosure.
Figure 5:
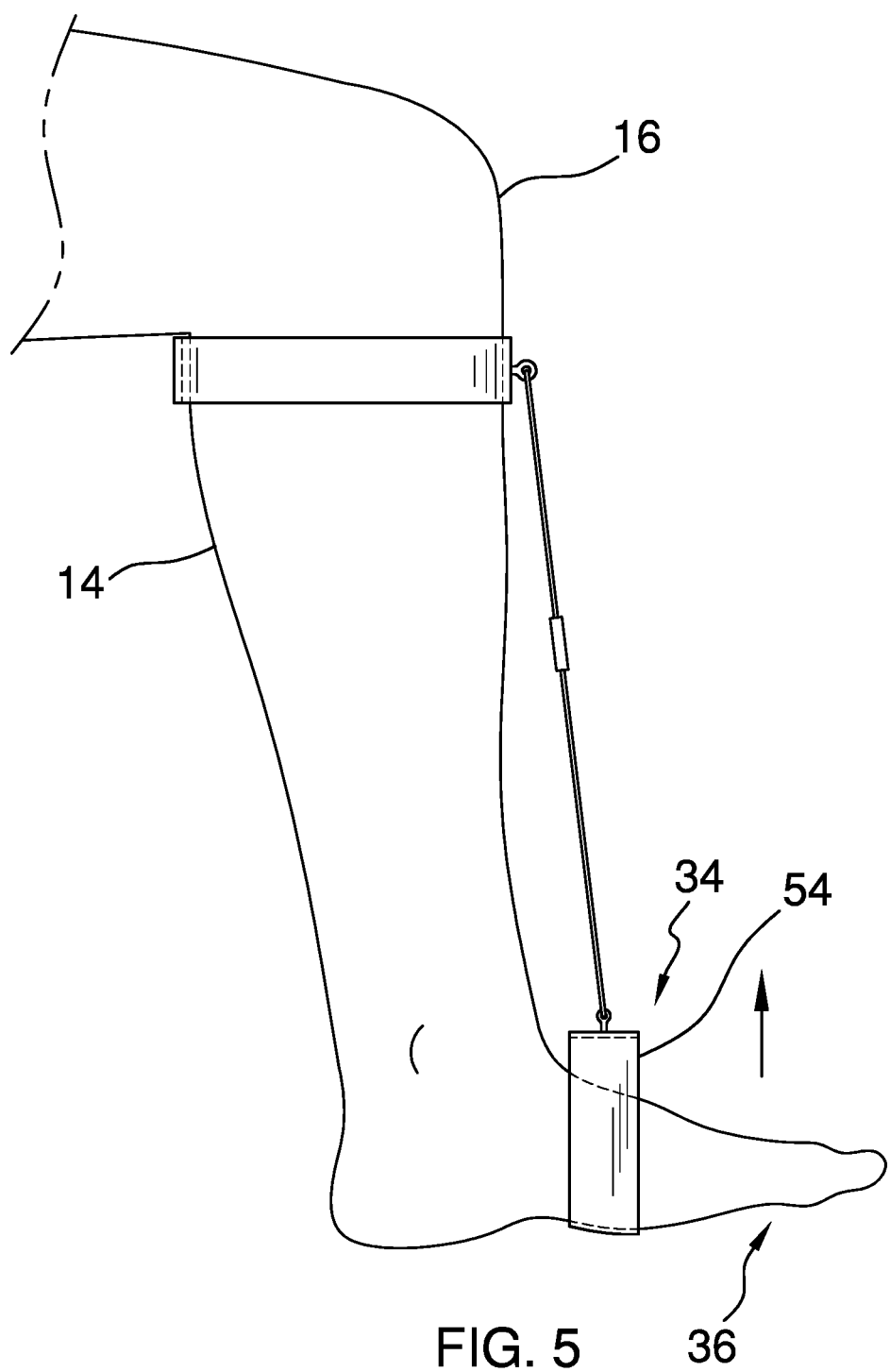
FIG. 5 is a side in-use view of an embodiment of the disclosure.

An engagement member 34 is attached to the second end 26 of the tether 22. The engagement member 34 is configured to engage a person's foot 36 to pull the foot 36 upwardly towards the knee 16. The engagement member 34 may include a conventional clip 38 having a first grip 40 and a second grip 42 biased away from each other. A first set of prongs 44 is attached to the first grip 40 and a second set of prongs 46 is attached to the second grip 44. Each of the first 44 and second 46 sets of prongs includes at least two prongs. The prongs 44, 46 each have a terminal end 48 and each of the terminal ends 48 is configured to be extended through a shoelace hole 50 in a shoe 52 positioned on the foot 36. Thus, the clip 38 engages the shoe 52 as shown in FIG. 4. Alternatively, as shown in FIG. 5, the engagement member 34 may include a strap 54 that is wrapped around the foot 36 directly and would typically be used when the foot 36 is bare.

Figure 3:
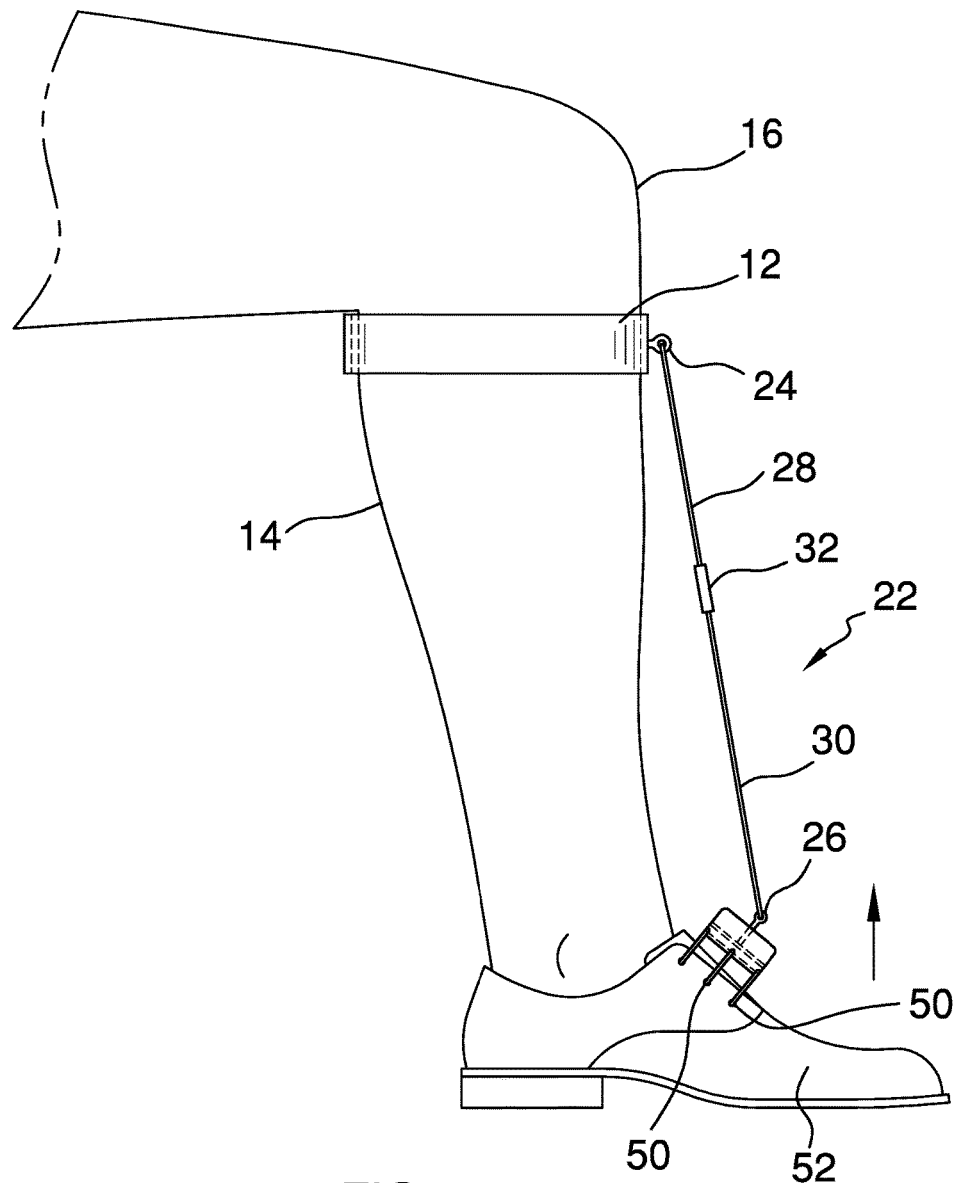
FIG. 3 is a side in-use view of an embodiment of the disclosure.

In use, the band 12 is wrapped around and secured to the leg 14 as shown in FIG. 3. The engagement member 34 then engages either the foot 36 directly or by way of the shoe 52 so that the tether 22 pulls the front portion of the foot 36 upwardly to prevent toes of the foot 36 to not drag on the ground during a forward step. Typically a person having foot drop requires the use of a cane or a heavy brace. The assembly 10 is more comfortable to wear and can be more easily retrofitted comparted to a complex brace apparatus.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A foot lifting assembly configured to lift a person's foot upwardly to counteract a drop foot condition, said assembly comprising:
   a band being configured to extend around a person's leg below and adjacent to a knee of the leg;
   a tether having a first end and a second end, said first end being attached to said band;
   an engagement member being attached to said second end of said tether, said engagement member being configured to engage a person's foot to pull the foot upwardly towards the knee; and
   wherein said engagement member includes a clip having a first grip and a second grip, a first set of prongs being attached to said first grip and a second set of prongs being attached to said second grip, each of said first and second sets of prongs including at least two prongs, each of said prongs having a terminal end, each of said terminal ends being configured to be extended through a shoelace hole in a shoe positioned on the foot.

2. The foot lifting assembly according to claim 1, wherein said band is formed into a closed loop configuration having an adjustable circumference.

3. The foot lifting assembly according to claim 2, wherein said band has a pair of free ends, a coupler being attached to said band and being configured to retain said band in said closed loop configuration.

4. The foot lifting assembly according to claim 1, wherein said tether is resiliently stretchable.

5. A foot lifting assembly configured to lift a person's foot upwardly to counteract a drop foot condition, said assembly comprising:
   a band being configured to extend around a person's leg below and adjacent to a knee of the leg, said band being formed into a closed loop configuration having an adjustable circumference, said band having a pair of free ends, a coupler being attached to said band and being configured to retain said band in said closed loop configuration;
   a tether having a first end and a second end, said first end being attached to said band, said tether being resiliently stretchable; and
   an engagement member being attached to said second end of said tether, said engagement member being configured to engage a person's foot to pull the foot upwardly towards the knee, said engagement member including a clip having a first grip and a second grip, a first set of prongs being attached to said first grip and a second set of prongs being attached to said second grip, each of said first and second sets of prongs including at least two prongs, each of said prongs having a terminal end, each of said terminal ends being configured to be extended through a shoelace hole in a shoe positioned on the foot.

* * * * *